(12) United States Patent
Becher et al.

(10) Patent No.: US 7,011,843 B2
(45) Date of Patent: Mar. 14, 2006

(54) METHOD FOR PROTECTING A HUMAN BEING AGAINST HEALTH IMPAIRMENT BY INGESTION OF A TRANSDERMAL THERAPEUTIC SYSTEM

(75) Inventors: Frank Becher, Koblenz (DE); Ann-Katrin Klink, Waldesch (DE)

(73) Assignee: LTS Lohmann-Therapie Systeme AG, Andernach (DE)

( * ) Notice: Subject to any disclaimer, the term of this patent is extended or adjusted under 35 U.S.C. 154(b) by 248 days.

(21) Appl. No.: 10/152,413

(22) Filed: May 21, 2002

(65) Prior Publication Data

US 2002/0187183 A1 Dec. 12, 2002

Related U.S. Application Data

(63) Continuation-in-part of application No. 09/486,214, filed on May 3, 2000, now abandoned, which is a continuation-in-part of application No. PCT/EP98/05955, filed on Sep. 18, 1998.

(30) Foreign Application Priority Data

Oct. 1, 1997 (DE) ................................ 197 43 484

(51) Int. Cl.
*A61F 13/00* (2006.01)
*A61L 15/16* (2006.01)

(52) U.S. Cl. ...................................... 424/449; 424/448

(58) Field of Classification Search ................ 424/449, 424/448
See application file for complete search history.

(56) References Cited

U.S. PATENT DOCUMENTS

| | | | |
|---|---|---|---|
| 3,947,570 A | 3/1976 | Pensak et al. | |
| 4,097,607 A | 6/1978 | Larson | |
| 4,438,046 A | 3/1984 | Grew et al. | |
| 5,149,538 A | 9/1992 | Granger et al. | |
| 5,236,714 A | 8/1993 | Lee et al. | |
| 5,891,919 A * | 4/1999 | Blum et al. | 514/625 |
| 5,939,095 A | 8/1999 | Hille et al. | |

FOREIGN PATENT DOCUMENTS

| | | |
|---|---|---|
| CA | 2114537 | 7/1992 |
| EP | 0 336 543 | 2/1989 |
| WO | WO 89/07959 | 9/1989 |
| WO | WO 90/04965 | 5/1990 |

* cited by examiner

*Primary Examiner*—Thurman K. Page
*Assistant Examiner*—Isis Ghali
(74) *Attorney, Agent, or Firm*—D. Peter Hochberg; Sean Mellino; Katherine R. Vieyra

(57) ABSTRACT

A method for the protection of a human being against any health impairment as a result of the ingestion of the whole or parts of a transdermal therapeutic system containing at least one pharmacologically active ingredient, which is toxic or induces nausea or addiction at oral, but not at transdermal administration is disclosed. The method comprises adding to said transdermal therapeutic system a substance being able to keep off a human being from said ingestion.

11 Claims, No Drawings

METHOD FOR PROTECTING A HUMAN BEING AGAINST HEALTH IMPAIRMENT BY INGESTION OF A TRANSDERMAL THERAPEUTIC SYSTEM

This is a continuation-in-part application of application Ser. No. 09/486,214 filed May 3, 2000 now abandoned, which is a continuation-in-part of PCT/EP98/05955, filed Sep. 18, 1998.

BACKGROUND OF THE INVENTION

1. Field of the Invention

The present invention relates to a method for the protection of a human being against any health impairment as a result of the ingestion of the whole or parts of a transdermal therapeutic system (TTS). More specifically, the present invention relates to a method for the protection of a human being against any health impairments as a result of the ingestion of the whole or parts of a transdermal therapeutic system, comprising at least one pharmacologically active ingredient-containing, especially a pressure-sensitive adhesive layer and at least on active-ingredient-impermeable backing layer, and further comprising a substance, which does not interact with the pharmacologically active ingredient and is able to keep off a human being from said ingestion.

2. Description of the Prior Art

A series of transdermal therapeutic systems present an acute danger of undesired side effects if administered orally by a human being in order to extract a soluble active agent. This is true whether the system is a new one or a used one. For example, infants have a tendency to stick anything interesting into their mouths and to at least suck or chew on it. This cannot be avoided especially if children happen to attain access to such systems by chance, especially systems with a release liner.

Such incidents have not yet been known to occur, but the pharmaceutical authorities increasingly fear that they might and have therefore, in various instances, demanded childproof packages. Such childproof packages have, in fact, been developed in various embodiments. However, they do not protect a child from putting a TTS in his or her mouth once the package has been opened or if the child somehow gets hold of a used patch. Especially in the case of a TTS with active substances such as anesthetics, analgesics, tranquilizers, or psychopharmacological agents, an oral abuse can lead to serious health impairments. On the other hand, addicts could be tempted to extract such active agents from transdermal therapeutic systems by means of sucking or chewing.

It is known that drinkable ethyl alcohol can be denatured and then put on the market as a methylated spirit in order to keep off people to drink it. A corresponding treatment of pharmaceutical dosage forms, particularly transdermal therapeutic systems, on the other hand, has not yet been published.

SUMMARY OF THE INVENTION

It is an object of the present invention to develop a method for the protection of a human being in a way that makes an oral abuse of the kind mentioned above impossible.

It is another object of the present invention to avoid a disadvantageous change in the transdermal therapeutic system's pharmacologically active ingredient.

To achieve these objects, the method according to the present invention proposes the addition of a pharmacologically neutral, non-interacting substance with a disgusting taste, with an irritating effect on the tongue and/or the oral mucosa of a human being, or with the property to induce nausea. Because this substance causes extremely unpleasant and unexpected experiences with respect to taste or causes nausea, a first oral contact with the TTS according to the present invention is sufficient for achieving a spontaneous reaction with the effect of immediately spitting out the corresponding patch. Thus, the present invention prevents children or drug addicts from an improper, i.e. oral, application of the active substance contained in the patch.

These and other objects of the invention may occur to those skilled in the art from the description to follow and from the appended claims.

DETAILED DESCRIPTION OF THE INVENTION

One embodiment of the present invention provides that a substance is used for the addition to a transdermal therapeutic system which causes nausea and thus spoils the temptation of oral application for the person concerned.

Another embodiment of the method according to the present invention provides that the substance is applied on top of the active substance-containing layer in a separate, extremely thin layer which does not prevent the permeation of the active substance. This has the benefit that the experiencing of an extremely disgusting taste directly upon first contact of the TTS with the oral mucosa or the tongue will dissuade further oral contact.

As a further measure, the substance can additionally be applied to the backing layer in a separate, preferably very thin layer, thus safely achieving a further intensification of the effect of denaturation.

In this case, the separate substance layer is to be applied in a thickness of between 10 and 100 $\mu$m, preferably between 5 and 20 $\mu$m.

An especially advantageous embodiment of the invention further provides for the use of a substance which causes an irritation such as a burning of the oral mucosa and the tongue. One such negative experience should suffice to lastingly dissuade a child or an addict from further attempts at oral contact with a TTS. A similar effect can also be achieved if a substance is used which causes an intensely bitter taste and especially an aftertaste.

An effective embodiment of the method according to the present invention provides for the use of substances selected from the group consisting of gallic acid, quinine, tannin, angostura, caffeine, lobeline, tea tree oil, certain hyphomycete cultures, denatured or coagulated substances, turpentine or ammonia as amaroids having a disgusting taste and/or irritating effect on the tongue and/or mucosa of a human being, and the use of emetine being able to induce nausea.

The above substances can be added to one or more layers of a TTS in a relative wide range of amount, depending on the kind of the properties of the substances.

An embodiment of the method according to the present invention provides that a substance having a disgusting taste and/or an irritating effect on the tongue or mucosa are applied in an amount of from 0.1 to 1.5 g, preferably in an amount of from 0.2 to 0.8 g to a single TTS.

Another embodiment of the method according to the present invention provides, that substances causing nausea, particularly emetine, are applied in an mount from 0.01 to 0.1 g, preferably in an amount of from 0.02 to 0.05 g to a single TTS.

For the implementation of one embodiment of the method, the invention provides for the incorporation of the substances in a film layer with which pharmacologically active-ingredient containing layer and, depending on the case, also the backing layer are coated. An especially advantageous solution provides for the use of a film layer soluble in saliva.

The method is uncomplicated and effective and protects children and/or addicts against health impairment by ingestion of the whole or parts of a transdermal therapeutic system. Thus, the method and the TTS according to the present invention present an ideal means of achieving the objects as mentioned above.

The invention has been described in detail, with particular emphasis having been placed on the preferred embodiments, but variations and modifications within the spirit and scope of the invention may occur to those skilled in the art to which it pertains.

We claim:

1. A method for dissuading a human being from the oral administration of the whole or parts of a transdermal therapeutic system having a layer containing at least one pharmacologically active ingredient, which is toxic and/or causes addiction at oral, but not transdermal, administration, which comprises applying on the top of the layer containing the at least one pharmacologically active ingredient, at least one separate thin film layer being soluble in saliva and containing an effective amount of a substance, which does not interact with said pharmacologically active ingredient, and causes the immediate spitting out of said transdermal therapeutic system after oral contact due to an adverse, disgusting or bitter taste and/or an irritating effect on the oral mucosa and/or tongue of a human being, said substance being selected from the group consisting of gallic acid, quinine, tannin, caffeine, lobeline, tea tree oil, hyphomycete cultures, turpentine and angostura.

2. The method according to claim 1, wherein the transdermal therapeutic system further comprises a pressure-sensitive adhesive layer and at least one backing layer being impermeable to the pharmacologically active ingredient.

3. The method according to claim 2, wherein the pharmacologically active ingredient containing layer and the pressure-sensitive adhesive layer are identical.

4. The method according to claim 1, wherein said film layer has a thickness of between 10 and 100 μm.

5. The method according to claim 2, wherein a thin film layer is additionally applied to said backing layer.

6. The method according to claim 5, wherein said film layer has a thickness of between 10 and 100 μm.

7. The method according to claim 1, wherein the thin film layer contains said substance in an amount of from 0.1 to 1.5 g.

8. The method according to claim 7, wherein the thin film layer contains said substance in an amount of from 0.2 to 0.8 g.

9. The method according to claim 8, wherein the thin film layer contains said substance in an amount of from 0.01 to 0.1 g.

10. The method according to claim 9, wherein the thin film layer contains said substance in an amount of from 0.02 to 0.05 g.

11. The method according to claim 1, wherein said pharmacologically active ingredient is selected from the group consisting of anesthetics, analgesics, tranquilizers and psychoactive drugs.

* * * * *